US008647577B2

(12) United States Patent
Hinz et al.

(10) Patent No.: US 8,647,577 B2
(45) Date of Patent: Feb. 11, 2014

(54) CHEMICAL COATING OF MICROWELL FOR ELECTROCHEMICAL DETECTION DEVICE

(71) Applicant: Life Technologies Corporation, Carlsbad, CA (US)

(72) Inventors: Wolfgang Hinz, New Haven, CT (US); John Matthew Mauro, Burlingame, CA (US); Shifeng Li, Fremont, CA (US); James Bustillo, Castro Valley, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 13/648,663

(22) Filed: Oct. 10, 2012

(65) Prior Publication Data

US 2013/0089466 A1    Apr. 11, 2013

Related U.S. Application Data

(63) Continuation of application No. 13/212,685, filed on Aug. 18, 2011, now abandoned.

(60) Provisional application No. 61/374,676, filed on Aug. 18, 2010.

(51) Int. Cl.
| | | |
|---|---|---|
| G01N 27/00 | (2006.01) | |
| G01N 27/30 | (2006.01) | |
| B05D 5/12 | (2006.01) | |
| B28B 19/00 | (2006.01) | |
| B29B 15/10 | (2006.01) | |
| C23C 18/00 | (2006.01) | |
| C23C 20/00 | (2006.01) | |
| C23C 24/00 | (2006.01) | |
| C23C 26/00 | (2006.01) | |
| C23C 28/00 | (2006.01) | |
| C23C 30/00 | (2006.01) | |
| H01C 17/06 | (2006.01) | |
| H05K 3/00 | (2006.01) | |
| H01L 21/00 | (2006.01) | |
| G01N 30/96 | (2006.01) | |

(52) U.S. Cl.
USPC ...... 422/82.01; 422/69; 422/82.03; 427/97.1; 427/97.7; 427/97.8; 436/94; 438/49

(58) Field of Classification Search
None
See application file for complete search history.

(56) References Cited

U.S. PATENT DOCUMENTS

| 4,683,195 A | 7/1987 | Mullis et al. |
| 4,683,202 A | 7/1987 | Mullis |

(Continued)

FOREIGN PATENT DOCUMENTS

| GB | 2461127 | 12/2009 |
| JP | 4262799 | 9/2004 |

(Continued)

OTHER PUBLICATIONS

Allen, Phillip E. et al., "CMOS Analog Circuit Design, Second Edition", *Oxford University Press*, 2002.

(Continued)

*Primary Examiner* — Jill Warden
*Assistant Examiner* — Julie Tavares

(57) ABSTRACT

The described embodiments may provide a method of fabricating a chemical detection device. The method may comprise forming a microwell above a CMOS device. The microwell may comprise a bottom surface and sidewalls. The method may further comprise applying a first chemical to be selectively attached to the bottom surface of the microwell, forming a metal oxide layer on the sidewalls of the microwell, and applying a second chemical to be selectively attached to the sidewalls of the microwell. The second chemical may lack an affinity to the first chemical.

20 Claims, 11 Drawing Sheets

(56) References Cited

U.S. PATENT DOCUMENTS

| | | | |
|---|---|---|---|
| 4,800,159 | A | 1/1989 | Mullis et al. |
| 4,965,188 | A | 10/1990 | Mullis et al. |
| 5,112,456 | A | 5/1992 | Worrell et al. |
| 5,126,022 | A | 6/1992 | Soane et al. |
| 5,210,015 | A | 5/1993 | Gelfand et al. |
| 5,399,491 | A | 3/1995 | Kacian et al. |
| 5,498,392 | A | 3/1996 | Wilding et al. |
| 5,587,128 | A | 12/1996 | Wilding et al. |
| 5,854,033 | A | 12/1998 | Lizardi |
| 5,858,195 | A | 1/1999 | Ramsey |
| 6,001,229 | A | 12/1999 | Ramsey |
| 6,010,607 | A | 1/2000 | Ramsey |
| 6,033,546 | A | 3/2000 | Ramsey |
| 6,054,034 | A | 4/2000 | Soane et al. |
| 6,174,670 | B1 | 1/2001 | Wittwer et al. |
| 6,399,952 | B1 | 6/2002 | Maher et al. |
| 6,613,525 | B2 | 9/2003 | Nelson et al. |
| 6,960,437 | B2 | 11/2005 | Enzelberger et al. |
| 7,049,645 | B2 | 5/2006 | Sawada et al. |
| 7,190,026 | B2 | 3/2007 | Lotfi et al. |
| 7,462,512 | B2 | 12/2008 | Levon et al. |
| 7,535,232 | B2 | 5/2009 | Barbaro et al. |
| 2006/0147983 | A1 | 7/2006 | O'uchi et al. |
| 2007/0059741 | A1 | 3/2007 | Kamahori et al. |
| 2007/0207471 | A1 | 9/2007 | Osaka et al. |
| 2008/0166727 | A1 | 7/2008 | Esfandyarpour et al. |
| 2008/0286762 | A1 | 11/2008 | Miyahara et al. |
| 2008/0286767 | A1 | 11/2008 | Miyahara et al. |
| 2009/0127589 | A1 | 5/2009 | Rothberg et al. |
| 2010/0052080 | A1 | 3/2010 | Garcia-Tello et al. |
| 2010/0137143 | A1 | 6/2010 | Rothberg et al. |
| 2010/0300895 | A1 | 12/2010 | Nobile et al. |
| 2012/0001235 | A1 | 1/2012 | Fife |
| 2012/0045368 | A1 | 2/2012 | Hinz et al. |

FOREIGN PATENT DOCUMENTS

| | | |
|---|---|---|
| WO | 99/19717 | 4/1999 |
| WO | 02/24322 | 3/2002 |

OTHER PUBLICATIONS

Anderson, E. et al., "A system for multiplexed direct electrical detection of DNA synthesis", *Sensors and Actuators B Chem.*, vol. 129, 2008, 79-86.
Baker, R J., "CMOS Circuit Design, Layout, and Simulation", *Wiley IEEE Press*, 2008.
Barbaro, M. et al., "Fully electronic DNA hybridization detection by a standard CMOS biochip", *Sensors and Actuators B Chemical*, vol. 118, 2006, 41-46.
Bard, Allen et al., "Electrochemical Methods: Fundamentals and Applications", *Wiley*, 2001.
Cao, Guozhong, "Nanostructures & Nanomaterials: Synthesis, Properties & Applications", *Imperial College Press*, 2004.
Dieffenbach, Carl (ED) et al., "PCR Primer: A Laboratory Manual, Second Edition" *Cold Spring Harbor Laboratory Press*, 2003.
Doering, Robert (ED) et al., "Handbook of Semiconductor Manufacturing Technology, Second Edition", *CRC Press*, 2007.
Elwenspoek, M et al., "Silicon Micromachining", *Cambridge University Press*, (2004 edition is paperback version of 1998 hardcover edition), 2004.
Hammond, P. et al., "Design of a Single-Chip pH Sensor Using a Conventional 0.6—μm CMOS Process", *IEEE Sensors Journal*, vol. 4(6), 2004, 706-712.
Heer, F et al., "Single-chip microelectronic system to interface with living cells" *Biosensors and Bioelectronics*, vol. 22, 2007, 2546-2553.
Hizawa, T et al., "Fabrication of a two-dimensional pH image sensor using a charge transfer technique", *Sensors and Actuators B Chemical*, vol. 117, 2006, 509-515.
Hughes, R C. et al., "Chemical Microsensors", *Science*, vol. 254, 1991, 74-80.
Levinson, Harry, "Principles of Lithography, Second Edition", *SPIE Press Monograph* vol. PM146, 2005.
Martinoia, S. et al., "Development of ISFET Array-Based Microsystems for Bioelectrochemical measurements of cell populations" *Biosensors & Bioelectronics*, vol. 16, 2001, pp. 1043-1050.
Milgrew, M. et al., "A large transistor based sensor array chip for direct extracellular imaging", *Sensors and Actuators B Chemical*, vol. 111-112, 2005, 347-353.
Milgrew, M. et al., "The development of scalable sensor arrays using standard CMOS technology", *Sensors and Actuators B*, vol. 103, 2004, 37-42.
Mir, Monica et al., "Integrated electrochemical DNA biosensors for lab-on-a-chip devices", *Electrophoresis*, vol. 30, 2009, 3386-3397.
Ohmori, Kazuyuki et al., "Performance of Cu Dual-Damascene Interconnects Using a Thin Ti-Based Self-Formed Barrier Layer for 28nm Node and Beyond", *Japanese Journal of Applied Physics*, vol. 49(05FD01), 2010, 1-4.
PCT/US2011/48268, International Search Report mailed Jan. 6, 2012.
PCT/US2011/48268, Written Opinion mailed Jan. 6, 2012.
Saliterman, Steven , "Fundamentals of BioMEMS and Medical Microdevices", *SPIE Press, Wiley-Interscience*, 2006.
Sawyer, Donald T. et al., "Electrochemistry for Chemists, Second Edition", *Wiley-Interscience*, 1995.
Sia, S et al., "Microfluidic devices fabricated in poly(dimethylsiloxane) for biological studies", *Electrophoresis*, 24:, 2003, 3563-3576.
Trojanowicz, Marek, "Recent developments in electrochemical flow detections—A review Part I. Flow analysis and capillary electrophoresis", *Analytica Chimica Acta*, vol. 653, 2009, 36-58.
Unger, M et al., "Monolithic Microfabricated Valves and Pumps by Multilayer Soft Lithography", *Science*, 288:, 2000, 113-116.
Veendrick, Harry, "Deep-Submicron CMOS ICs: From Basics to ASICs", *Kluwer Academic Publishing*, 1998.
Xu, Xiaoli et al., "Integration of electrochemistry in micro-total analysis systems for biochemical assays: Recent developements", *Talanta*, vol. 80, 2009, 8-18.
Yeow, T.C.W. et al., "A very large integrated pH-ISFET sensor array chip compatible with standard CMOS processes", *Sensor and Actuators B*, vol. 44, 1997, 434-440.
Krause, M. et al., "Extended gate electrode arrays for extracellular signal recordings", Sensors and Actuators B, vol. 70, 2000, pp. 101-107.
PCT/US2011/048268 International Preliminary Report on Patentability dated Feb. 19, 2013.
PCT/US2013/021622, "International Search Report of the International Searching Authority and Written Opinion" dated May 14, 2013.

Fig. 2A
(Prior Art)
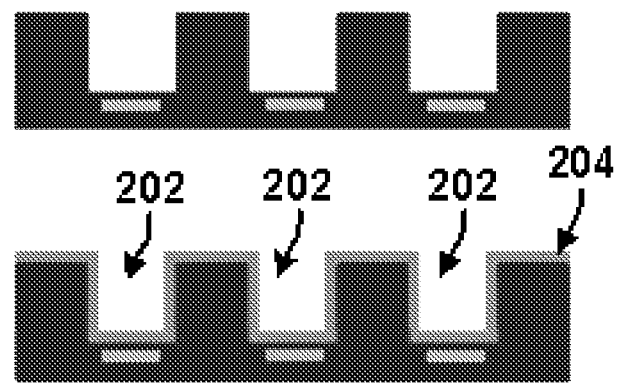
Fig. 2B
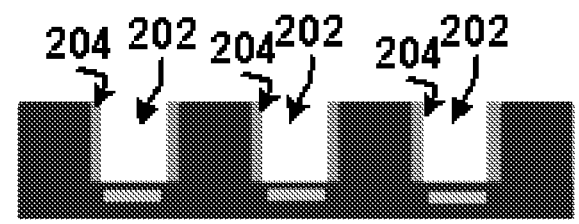
Fig. 2C

CHEMICAL COATING OF MICROWELL FOR ELECTROCHEMICAL DETECTION DEVICE

RELATED APPLICATIONS

This application is a continuation of U.S. patent application Ser. No. 13/212,685, which claims the benefit of priority to previously filed U.S. provisional patent application Ser. No. 61/374,676 filed Aug. 18, 2010, and incorporates the disclosures by reference intheir entirety.

This application also incorporates by reference in its entirety the U.S. patent application Ser. No. 12/785,716 filed May 24, 2010.

BACKGROUND

Electrochemical detection is attractive because it provides high sensitivity, small dimensions, low cost, fast response, and compatibility with microfabrication technologies. (See, e.g., Hughes et al., Science, 254: 74-80 (1991); Mir et al., Electrophoresis, 30: 3386-3397 (2009); Trojanowicz, Anal. Chim. Acta, 653: 36-58 (2009); and, Xu et al., Talanta, 80: 8-18 (2009).) These characteristics have led to the development of a variety of sensors based on amperometric, potentiometric or impedimetric signals and their assembly into arrays for chemical, biochemical and cellular applications. (See, e.g., Yeow et al., Sensors and Actuators B 44: 434-440 (1997); Martinoia et al., Biosensors & Bioelectronics, 16: 1043-1050 (2001); Hammond et al., IEEE Sensors J., 4: 706-712 (2004); Milgrew et al., Sensors and Actuators B 103: 37-42 (2004); Milgrew et al., Sensors and Actuators B, 111-112: 347-353 (2005); Hizawa et al., Sensors and Actuators B, 117: 509-515 (2006); Heer et al., Biosensors and Bioelectronics, 22: 2546-2553 (2007); Barbaro et al., Sensors and Actuators B, 118: 41-46 (2006); Anderson et al., Sensors and Actuators B, 129: 79-86 (2008); Rothberg et al., U.S. patent publication 2009/0127589; and, Rothberg et al., U.K. patent application GB24611127.) Typically in such systems, analytes are randomly distributed among an array of confinement regions, such as microwells (also referred to herein as "wells") or reaction chambers, and reagents are delivered to such regions by a fluidics system that directs flows of reagents through a flow cell containing the sensor array. Microwells in which reactions take place, as well as empty wells where no reactions take place, may be monitored by one or more electronic sensors associated with each of the microwells.

In one type of electrochemical detection, the fundamental reaction product, or "signal", is a pH change. The pH change is detected by measuring a change in the surface charge at the bottom of the well. The surface at the bottom of the well buffers the pH change produced as a result of the biological reaction. The resulting change in surface charge due to the biological reaction is sensed by capacitive coupling of the bottom of the well to a floating gate of a chemically-sensitive field effect transistor (chemFET) below the surface. However, the sidewalls of the well are too far removed from the chemFET to contribute to the chemFET signal. Unfortunately, in current implementations, the sidewalls of the well buffer as well as surface at the bottom of the well. For example, FIG. 2A shows a prior art microwell structure with native metal oxide, nitride, or oxinitride surface on both the bottom and sidewall. Hence the sidewall's buffering reduces the signal detected at the bottom of the well.

In view of the above, it would be advantageous to have available a microwell structure and a method of conformal coating and selective etching of microwell sidewalls that reduce sidewall buffering, which overcome the deficiencies of current approaches.

BRIEF DESCRIPTION OF THE DRAWING FIGURES

FIG. 2A illustrates a well structure of the prior art with a native metal oxide surface.

FIG. 2B illustrates a well structure with a conformal silanized surface according to an embodiment of the present teachings.

FIG. 2C illustrates a well structure with a conformal silanized surface, and all horizontal surfaces etched to the original metal oxide according to an embodiment of the present teachings.

FIGS. 9A-9E illustrate different stages of fabricating a well structure according to another embodiment of the present teachings.

DETAILED DESCRIPTION

The described embodiments may provide a chemical detection device with an improved signal-to-noise ratio (SNR). The chemical detection device may include a microwell coated with a chemical that binds to the bottom of the microwell and facilitates binding of an ion and a CMOS device placed underneath the bottom of the microwell. In different embodiments, the sidewalls of the microwell may be made of silicon dioxide ($SiO_2$) or plastic. In one embodiment, the sidewalls of the microwell may be coated with a silane group that reduces buffering of protons in solutions. The SNR may be improved by a reduction of buffering of protons by the sidewalls.

One embodiment may provide a method of fabricating a chemical detection device with an improved signal-to-noise ratio. The method may comprise forming a plastic layer on top of a CMOS device, forming a layer of metal oxide on top of the plastic layer, forming a microwell on the plastic layer on top of the CMOS device by anisotropic plastic etching, and applying a chemical that binds to the bottom of the microwell but does not bind to the plastic sidewall.

Another embodiment may provide a method of fabricating a chemical detection device with an improved signal-to-noise ratio. The method may comprise forming an opening of a microwell on a metal oxide layer on top of a silicon dioxide ($SiO_2$) layer. The $SiO_2$ layer may be on top of a CMOS device. The method may further comprise forming a circular undercut on the $SiO_2$ layer underneath an edge of the opening of the microwell, forming the microwell on the $SiO_2$ layer on top of the CMOS device by anisotropic $SiO_2$ etching, applying one chemical that binds to the sidewalls and at the bottom of the microwell, deactivating the chemical at the bottom of the microwell, and applying another chemical that locates at the bottom of the microwell and facilitates binding of ions.

A further embodiment may provide a method of fabricating a chemical detection device with an improved signal-to-noise ratio. The method may comprise forming a metal oxide layer on top of a silicon dioxide ($SiO_2$) layer. The $SiO_2$ layer may be on top of a CMOS device. The method may further comprise forming a microwell on the $SiO_2$ layer on top of the CMOS device, applying a chemical that binds to a sidewall and a bottom of the microwell, and etching away the chemical at the bottom of the microwell.

Another embodiment may provide a method of fabricating a chemical detection device with an improved signal-to-noise ratio. The method may comprise forming a microwell in a silicon dioxide ($SiO_2$) layer on top of a CMOS device, applying a chemical to be selectively attached to the bottom of the microwell, forming a metal oxide layer on the top edges and sidewalls of the microwell, and applying another chemical to be selectively attached to the top edges and sidewalls of the microwell.

Figure 1:
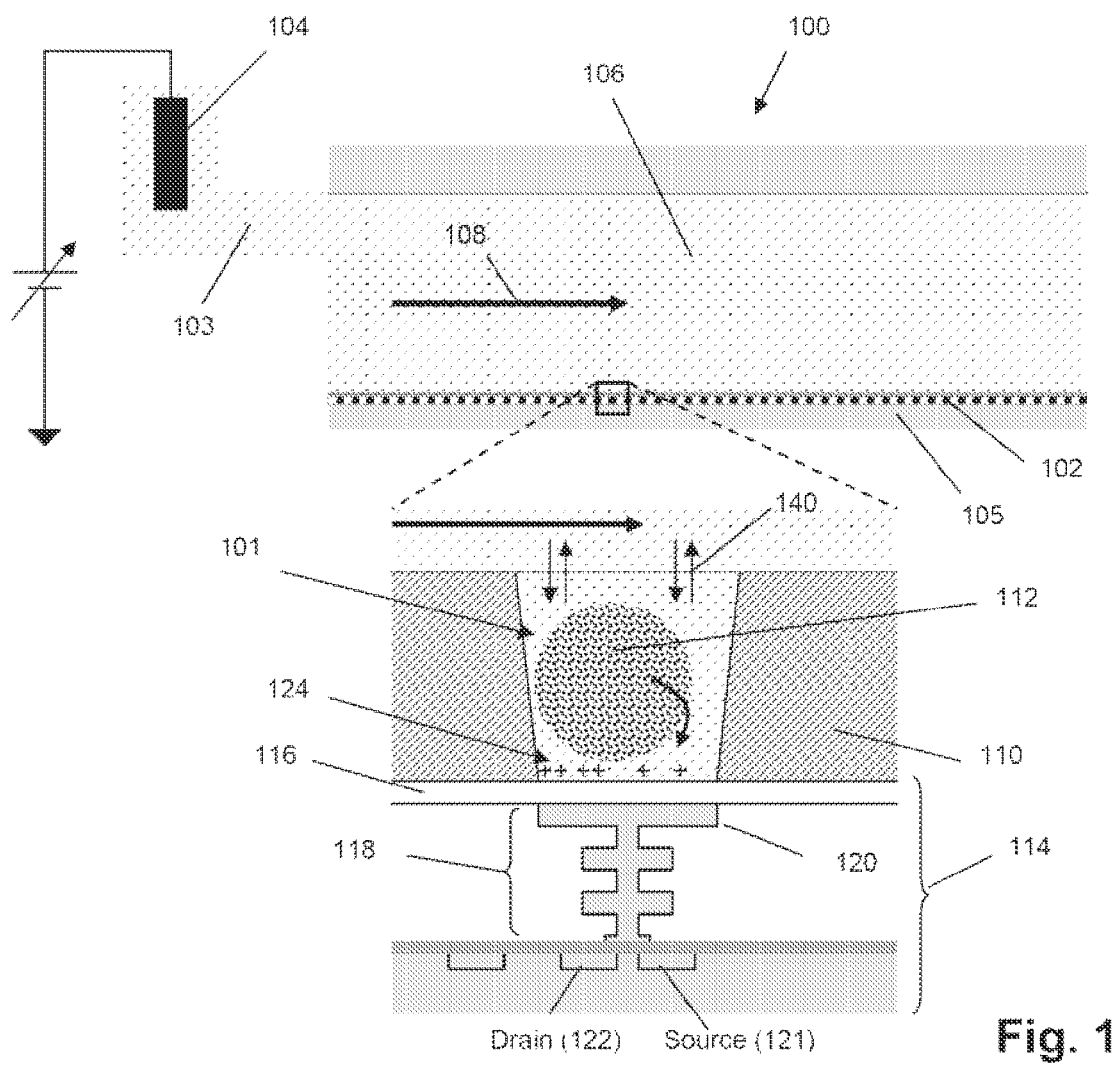
FIG. 1 illustrates a cross-sectional view of a flow cell according to an embodiment of the present teachings.

FIG. 1 is an expanded and cross-sectional view of flow cell 100 showing a portion of a flow chamber 106 with reagent flow 108 moving across the surface of microwell array 102 over the open ends of the microwells. Microwell array 102 and sensor array 105 together may form an integrated unit forming a bottom wall or floor of flow cell 100. In one embodiment, reference electrode 104 may be fluidly connected to flow chamber 106. A microwell 101 and sensor 114 are shown in an expanded view. Microwell 101 may be formed in the bulk material 110 by any conventional microfabrication technique. The volume, shape, aspect ratio (such as base width-to-well depth ratio), and other dimensional characteristics of the microwells may be design choices that depend on a particular application, including the nature of the reaction taking place, as well as the reagents, byproducts, and labeling techniques (if any) that are employed. The sensor 114 may be a chemFET with a floating gate 118 having a sensor plate 120 separated from the microwell interior by a passivation layer 116. The sensor 114 may be predominantly responsive to (and generates an output signal related to) the amount of charge 124 present on the passivation layer 116 opposite of the sensor plate 120. Changes in charge 124 may cause changes in the current between source 121 and drain 122 of the FET, which may be used directly to provide a current-based output signal or indirectly with additional circuitry to provide a voltage-based output signal. Reactants, wash solutions, and other reagents may move into microwells from flow chamber 106 primarily by diffusion 140.

In one embodiment, reactions carried out in microwell 101 may be analytical reactions to identify or determine characteristics or properties of an analyte of interest. Such reactions may generate directly or indirectly byproducts that affect the amount of charge adjacent the sensor plate 120. (Indirect detection may occur, for example, if byproduct chelators or other binding compounds are used that affect the sensor after binding an analyte of interest or if labeling moieties are employed, such as enzymes that may generate a secondary byproduct as the result of a binding event, or the like). If such byproducts are produced in small amounts or rapidly decay or react with other constituents, then multiple copies of the same analyte may be analyzed in microwell 101 at the same time in order to increase the output signal ultimately generated. In one embodiment, multiple copies of an analyte may be attached to a solid phase support 112, either before or after deposition into a microwell. The solid phase support 112 may be microparticles, nanoparticles, beads, solid and porous comprising gels, and the like. For nucleic acid analyte, multiple, connected copies may be made by rolling circle amplification (RCA), exponential RCA, and like techniques, to produce an amplicon without the need of a solid support.

In one embodiment, the byproduct produced as a result of genomic DNA fragment sequencing is a pH change due to the incorporation of a nucleotide. In an embodiment, this may occur at an appropriate operating pH of between 7.5 and 7.8. Approximately one proton is released per nucleotide that is incorporated under the given conditions. The pH change is detected by measuring the change in the charge of the surface on the bottom of the well. The surface on the bottom and the sides of a well are typically composed of a metal oxide or nitride. The surface may comprise a number of surface groups that undergo charging reactions. These charging reactions can be described using the equations below:

$$\text{M-OH} \leftrightarrow \text{M-O}^- + \text{H}^+ \tag{1}$$

$$\text{M-OH} + \text{H}^+ \leftrightarrow \text{M-OH}_2^+ \tag{2}$$

The number of surface groups, along with the characteristic equilibrium constants associated with the charging reactions above, impart a buffering capacity to the surface. The surface buffering capacity in a limited sample volume, such as a microwell, will buffer the pH change associated with the biological incorporation reaction. The change in surface charge due to the charging reactions (equations (1) and (2) above) may be sensed by capacitively coupling the bottom of the well to a chemFET located below the bottom surface of the well. As discussed in the Background section, however, the sidewalls of the well are too far removed from the chemFET to contribute to the chemFET signal. Therefore, embodiments of the present invention use conformal coating to differentiate the sidewalls and the bottom of the well, and thus reduce the sidewall buffering.

FIGS. 2B and 2C show one embodiment of the present invention which solves the problem of sidewall buffering by conformal coating of the native metal oxide, nitride, or oxinitride surface layer, followed by selective etching of all horizontal surfaces. FIG. 2B shows the conformal coating of all surfaces of the microwell with silane, in accordance with one embodiment of the present invention. As shown in FIG. 2B, microwells 202 may be covered (both on the bottom and sidewalls) by a layer 204. The layer 204, for example, may be a layer of chemical that lacks an affinity for protons. The conformal coating reduces or eliminates surface groups that can undergo reactions with protons in solution and hence reduces or eliminates the buffering capacity of said surfaces. For example, when the layer 204 is removed from the bottom of the microwells 202, the layer 204 on the sidewalls may help reduce or eliminate buffering capacity of the sidewalls of the microwells. FIG. 2C shows the results of the selective etching of horizontal surfaces only (including the bottom of the wells and top edges between wells), restoring the native metal oxide, nitride, or oxinitride surface, and hence allows the pH sensing to occur selectively at the bottom of the well. Different techniques for etching the horizontal surfaces can be employed. In an embodiment, the etching is accomplished using a directional reactive ion etch of the horizontal surfaces (e.g., Bosch process).

Figure 3A:
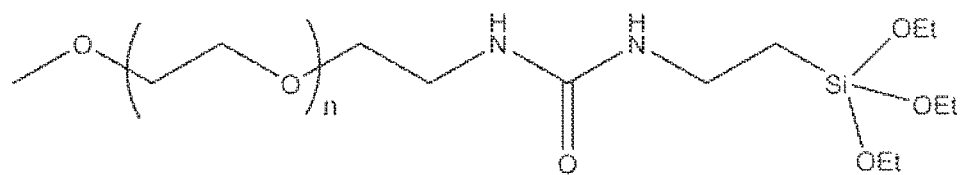
FIG. 3A illustrates the molecular structure of a PEG-Silane of one type of silane that can be used for the conformal coating process of the microwells according to an embodiment of the present teachings.
Figure 3B:
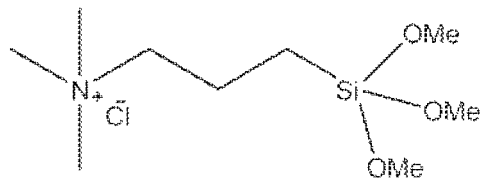
FIG. 3B illustrates the molecular structure of another type of silane that can be used for the conformal coating process of the microwell according to an embodiment of the present teachings.
Figure 3C:
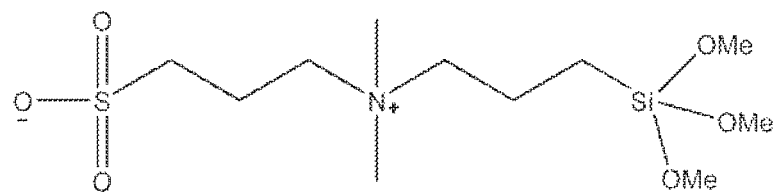
FIG. 3C illustrates the molecular structure of a zwitter ionic species silane that can be used for the conformal coating process of the microwells according to an embodiment of the present teachings.

FIGS. 3A-3C shows different types of silane that can be used for the conformal coating process. FIG. 3A shows the structure of PEG-Silane that can be used in the conformal coating process. It may be available from NANOCS.com (Product code PEG6-0 I 02) and has an average MW of PEG=2000. It may impart a hydrophilic surface that does not change in charge with small changes in pH around the operating pH (e.g., pH range of 7.5 to 7.8). FIG. 3B shows the structure of N,N,N-trimethyl-3-(trimethoxysilyl)-I-propan-aminium chloride silane that can be used in the conformal coating process. It may be available from Sigma Aldrich (Product # 595888). It may impart a hydrophilic positive charge to all vertical surfaces. The charge on the surface does not respond to small changes in pH around the operating pH. FIG. 3C shows the structure of a zwitter ionic species silane that can be used in the conformal coating process. It is available in a single step reaction using propane sultone and APTMS. It may impart a highly hydrophilic but overall neutral coating to the sidewalls.

Figure 4A:
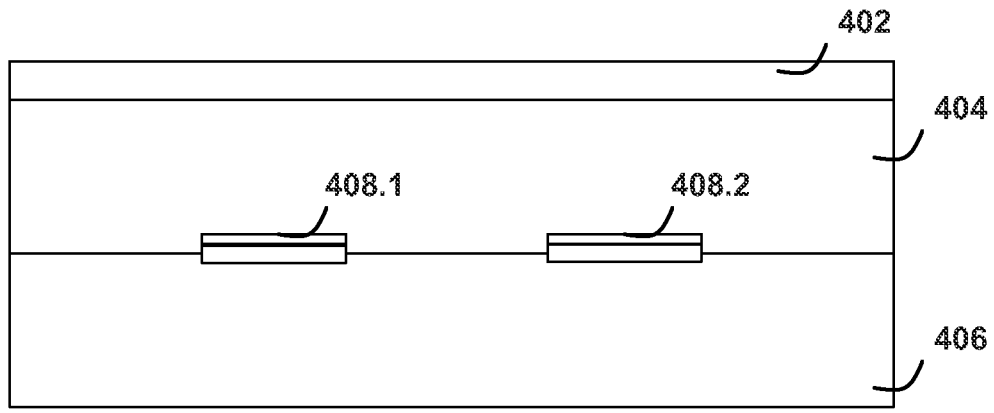
FIGS. 4A-4C illustrate different stages of fabricating a well structure according to an embodiment of the present teachings.
Figure 4B:
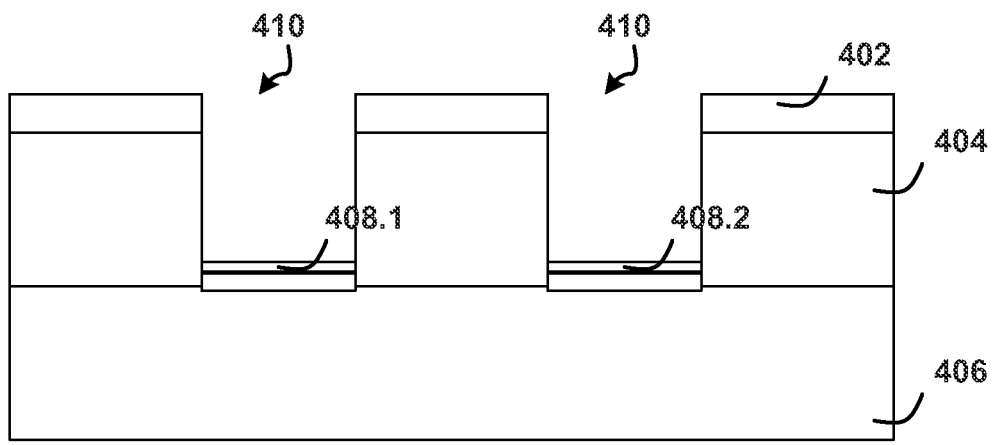
Figure 4C:
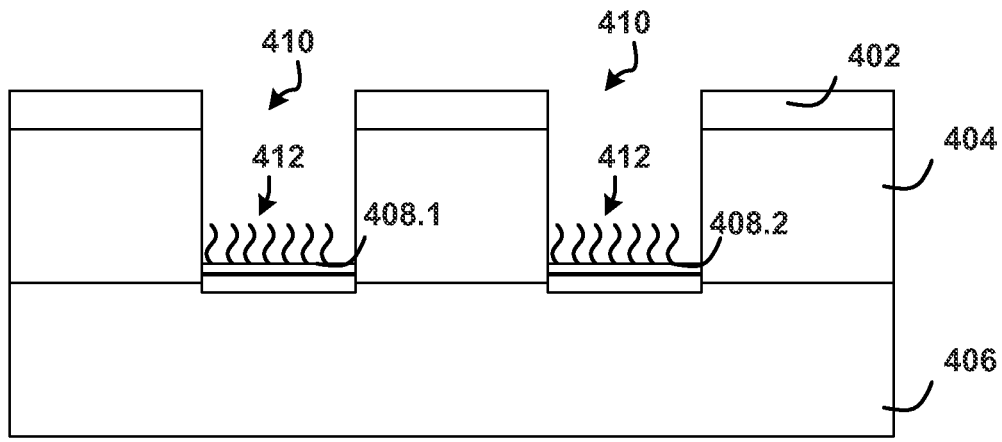

FIGS. 4A-4C illustrate cross-sectional views of different stages of fabricating a well structure according to an embodiment of the present teachings. FIG. 4A shows a cross-sectional view of a part of a chemical sensing device 400 before microwells are formed. The chemical sensing device 400 may comprise a metal oxide layer 402, a microwell layer 404, a CMOS device layer 406 and charge sensitive devices 408.1 and 408.2 between the microwell layer 404 and the CMOS device layer 406. The metal oxide layer 402 may be on top of the microwell layer 404, which in turn may be on top of the CMOS device layer 406. The charge sensitive devices 408.1 and 408.2 may each represent a top portion of a chemFET. For example, the charge sensitive devices 408.1 and 408.2 may be the passivation layers of the chemFETs (e.g., passivation layer 116 of FIG. 1), while the floating gate structures of the chemFETs may be underneath the charge sensitive devices 408.1 and 408.2 (not shown). In one embodiment, the microwell layer 404 may be a layer of plastic (e.g., Cytop, TEFLON, Parylene, etc.). Further, in one embodiment, the charge sensitive devices 408.1 and 408.2 may each comprise two or more layers of metal oxides. For example, each of the charge sensitive devices 408.1 and 408.2 may comprise a top layer of tantalum pentoxide ($Ta_2O_5$) and a bottom layer of aluminum oxide ($Al_2O_3$). The metal oxide layer 402 may comprise one or more layers of $Ta_2O_5$, Hafnium dioxide ($HfO_2$), zirconium oxide ($ZrO_2$), or $Al_2O_3$. The CMOS device layer may be a layer of semiconductor material (e.g., Si).

FIG. 4B shows a cross-sectional view of the chemical sensing device 400 with a pair of microwells 410. The microwells 410 may be etched on the metal oxide layer 402 and the microwell layer 404. In one embodiment, the microwells 410 may be etched to expose the top of the charge sensitive devices 408.1 and 408.2. The microwells 410 may be etched, for example, by anisotropic etching. FIG. 4C shows a cross-sectional view of the chemical sensing device 400 after a chemical may be applied to it. The applied chemical, shown as wiggly lines 412, may be coated only at the bottom of the microwells because of inert property of the plastic sidewall. In one embodiment, the plastic sidewalls may have zero buffering because of the inert property. In one embodiment, the chemical may be phosphate, phosphonate, or silane.

Figure 5:
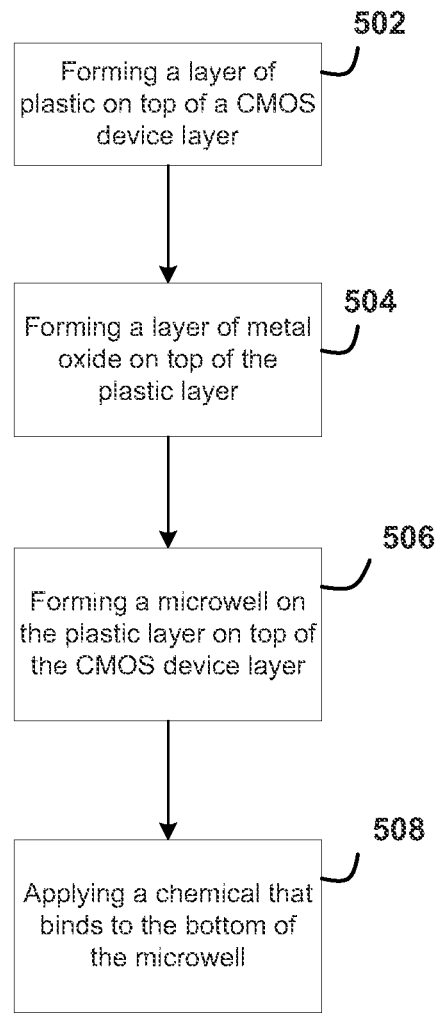
FIG. 5 illustrates a process of fabricating a well structure of FIG. 4C according to an embodiment of the present teachings.

FIG. 5 illustrates a process 500 of fabricating a well structure of FIG. 4C according to an embodiment of the present teachings. At block 502, the process 500 may form a layer of plastic on top of a CMOS device layer. As shown in FIG. 4A, the plastic layer 404 may be formed on top of the CMOS device layer 406. Then at block 504, the process 500 may form a layer of metal oxide on top of the plastic layer. For example, the metal oxide layer 402 may be formed on top of the plastic layer 404 in FIG. 4A. The process 500 may then proceed to block 506. At block 506, a microwell may be formed on the plastic layer on top of the CMOS device layer. As described above with respect to FIG. 4B, the etching on the plastic layer may be performed by anisotropic plastic etching. At block 508, a chemical may be applied. The chemical (e.g., the wiggly lines 412) may bind only to the bottom of the microwell, for example, because of the inert property of the plastic sidewall.

Figures 6A, 6B:
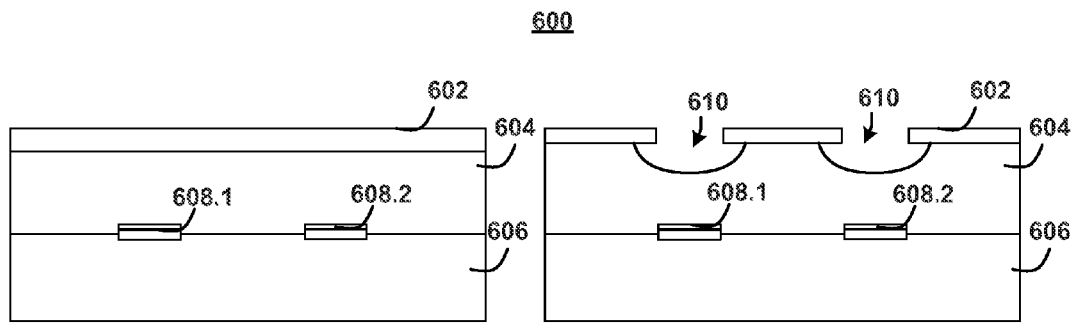
FIGS. 6A-6F illustrate different stages of fabricating another well structure according to an embodiment of the present teachings.

FIGS. 6A-6F illustrate cross-sectional views of different stages of fabricating a well structure according to another embodiment of the present teachings. FIG. 6A shows a cross-sectional view of a part of a chemical sensing device 600 before microwells are formed. The chemical sensing device 600 may comprise a metal oxide layer 602, a microwell layer 604, a CMOS device layer 606 and charge sensitive devices 608.1 and 608.2 between the microwell layer 604 and the CMOS device layer 606. The metal oxide layer 602 may be on top of the microwell layer 604, which in turn may be on top of the CMOS device layer 606. The charge sensitive devices 608.1 and 608.2 may each represent a top portion of a chemFET. For example, the charge sensitive devices 608.1 and 608.2 may be the passivation layers of the chemFETs (e.g., passivation layer 116 of FIG. 1), while the floating gate structures of the chemFETs may be underneath the charge sensitive devices 608.1 and 608.2 (not shown). In one embodiment, the microwell layer 604 may be a layer of silicon oxide ($SiO_2$). Further, in one embodiment, the charge sensitive devices 608.1 and 608.2 may each comprise two or more layers of metal oxides. For example, each of the charge sensitive devices 608.1 and 608.2 may comprise a top layer of $Ta_2O_5$ and a bottom layer of $Al_2O_3$. The metal oxide layer 602 may comprise one or more layers of $Ta_2O_5$, $HfO_2$, $ZrO_2$, or $Al_2O_3$. The CMOS device layer 606 may be a layer of semiconductor material (e.g., Si).

Figures 6C, 6D:
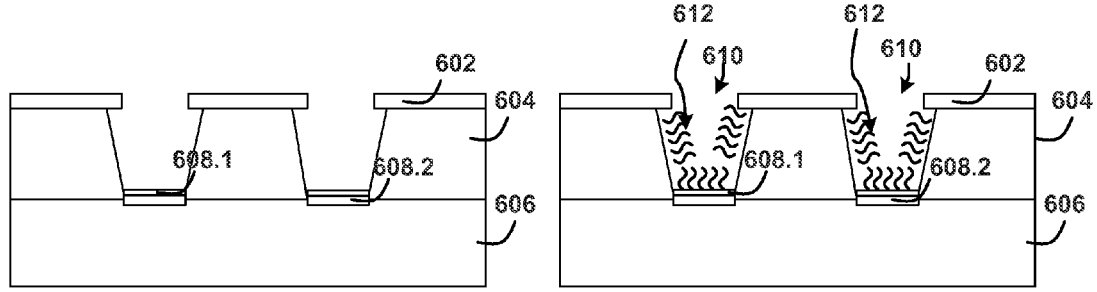

FIG. 6B shows a cross-sectional view of the chemical sensing device 600 with a pair of microwells 610 being formed. The openings of the microwells 610 may be etched on the metal oxide layer 602 and the upper portion of the microwell layer 604. As shown in FIG. 6B, underneath the opening edges of the metal oxide layer 602, upper portion of the microwell layer 604 may be etched to create undercuts. In one embodiment, the undercuts may be created by isotropic $SiO_2$ etching. FIG. 6C shows a cross-sectional view of the chemical sensing device 600 with the pair of microwells 610 having been formed. In one embodiment, the microwells 610 may be etched to expose the top of the charge sensitive devices 608.1 and 608.2. The microwells 610 may be formed by anisotropic $SiO_2$ etching. FIG. 6D shows a cross-sectional view of the chemical sensing device 600 after application of a chemical. The applied chemical, shown as wiggly lines 612, may be coated to cover sidewalls and bottom of the microwells 610. In one embodiment, the chemical may be a silane group.

Figures 6E, 6F:
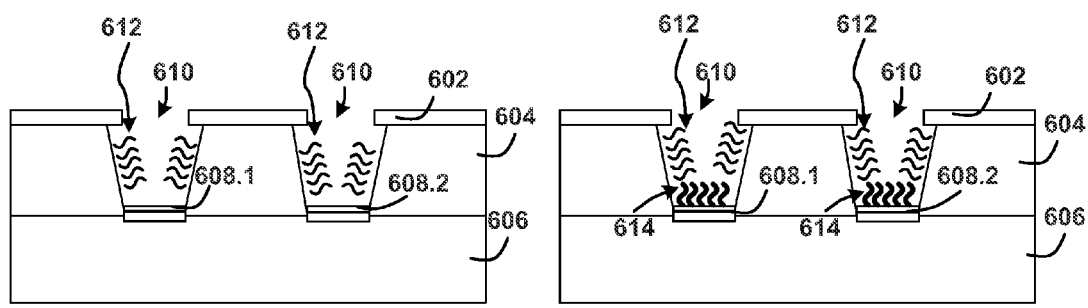

FIG. 6E shows a cross-sectional view of the chemical sensing device 600 with the bottom of the pair of microwells 610 having been cleaned of the applied chemical. In one embodiment, the microwells 610 may be etched to clean the applied chemical and expose the top of the charge sensitive devices 608.1 and 608.2. The bottom of the microwells 610 may be cleaned by directional etching, reactive ion etching, sacrificial layer etching, or combination of these etching techniques. If the sacrificial layer etching is used, a sacrificial layer may be created on top of the metal oxide sensing layers of the charge sensitive devices 608.1 and 608.2 before the chemical is applied. After the chemical is applied, the sacrificial layer may be etched to strip the chemical at the bottom of the microwells 610 to expose the metal oxide sensing layers of the charge sensitive devices 608.1 and 608.2. In another embodiment, the chemical may be deactivated by other means, such as, for example, covered or chemically rendered inactive.

FIG. 6F shows a cross-sectional view of the chemical sensing device 600 after application of another chemical. The other applied chemical, which may be referred to as the first chemical and shown as bolded wiggly lines 614, may be coated to cover the bottom of the microwells 610. In one embodiment, the other chemical may be one or more chemicals selected from a group including: phosphate, phosphonate, catechol, nitrocatechol, boronate, phenylboronate, imidazole, silanol or other pH-sensing group. The other chemical may be positively charged to help bead loading and help accumulation of electrical charges caused by chemical reactions.

In one embodiment, the other chemical may be absent. That is, the chemical sensing device 600 may have the sidewalls of microwells 610 coated with one group of chemicals and may leave the bottom of the microwells 610 exposed. By coating only the sidewalls with one group of chemicals, the buffering of electrical charges by the sidewalls may be reduced or eliminated, and the SNR may be improved.

Figure 7:
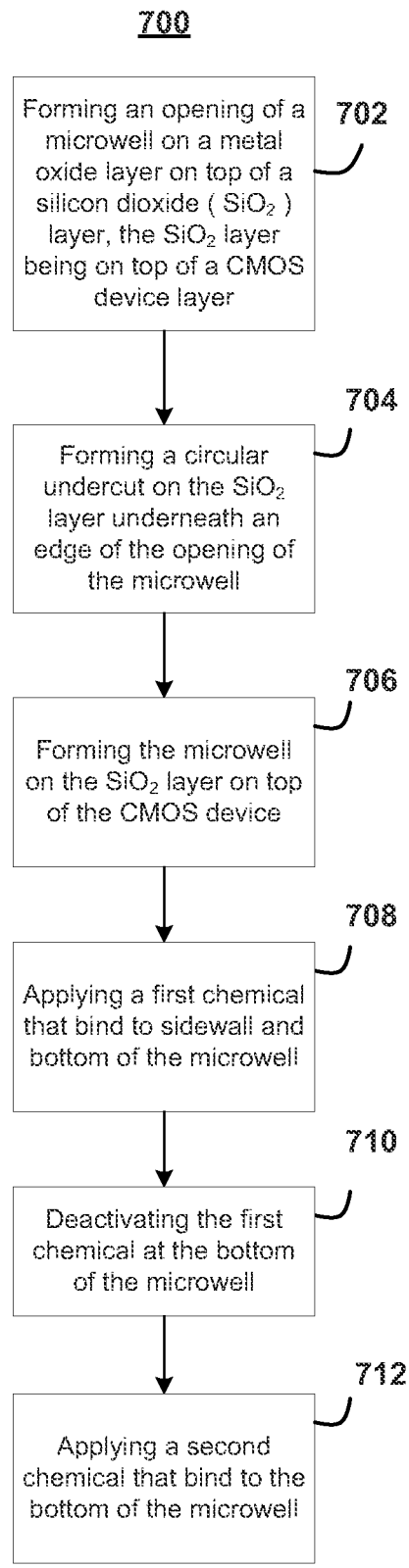
FIG. 7 illustrates a process of fabricating a well structure of FIG. 6F according to an embodiment of the present teachings.

FIG. 7 illustrates a process of fabricating a well structure of FIG. 6F according to an embodiment of the present teachings. At block 702, an opening of a microwell may be formed on a metal oxide layer on top of a silicon dioxide ($SiO_2$) layer and the $SiO_2$ layer may be on top of a CMOS device layer. Then at block 704, a circular undercut may be formed on the $SiO_2$ layer underneath an edge of the opening of the microwell. As shown in FIG. 6B, opening and undercuts around the opening for the microwells 610 may be formed on the metal oxide layer 602 and microwell layer 606. As described above with respect to FIG. 6B, the undercuts may be created by isotropic $SiO_2$ etching. At block 706, a microwell may be formed on the $SiO_2$ layer on top of the CMOS device layer. For example, anisotropic $SiO_2$ etching may be used to etch the microwells. At block 708, a chemical may be applied to the microwell. The chemical may bind to the sidewall and bottom of the microwell, and cover the sidewall and bottom of the microwell. At block 710, the chemical at the bottom of the microwell may be deactivated. For example, the chemical may be removed (e.g., by directional etching, reactive ion etching , sacrificial layer etching, or combination thereof), inactivated by chemicals, or covered. At block 712, another chemical may be applied to the microwell. The other chemical may bind to the bottom of the microwell and facilitate binding of ions.

Figure 8:
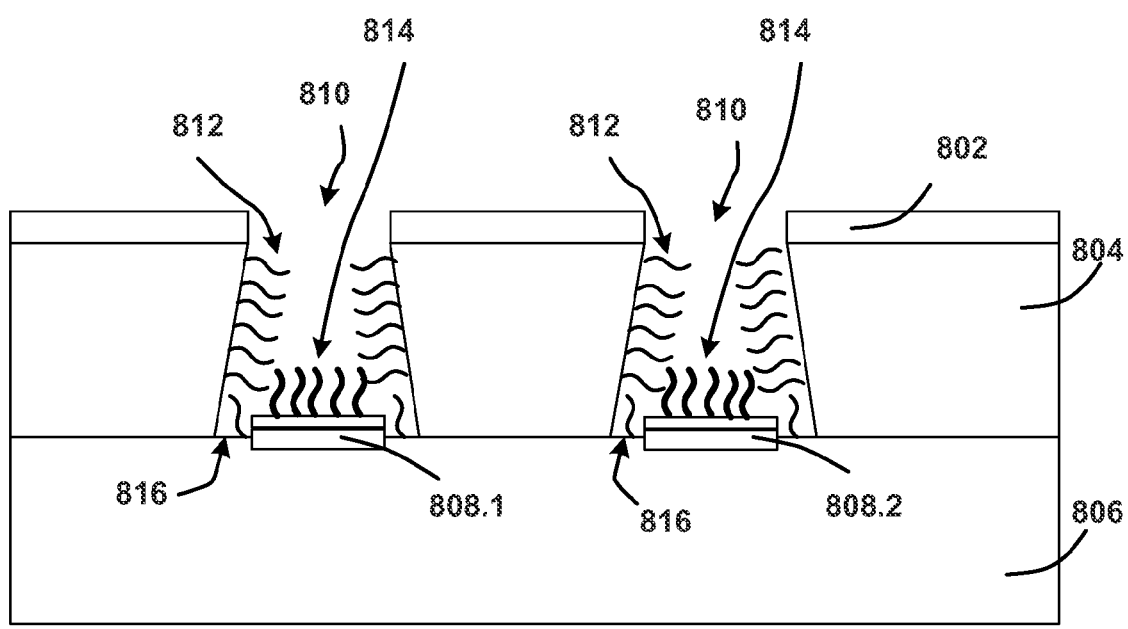
FIG. 8 illustrates a well structure according to another embodiment of the present teachings.

FIG. 8 illustrates a well structure according to another embodiment of the present teachings. The well structure of FIG. 8 may comprise a metal oxide layer 802, a microwell layer 804, a CMOS device layer 806 and a chemical sensing device 808.1 or 808.2. The metal oxide layer 802 may be on top of the microwell layer 804, which in turn may be on top of the CMOS device layer 806. The charge sensitive devices 808.1 and 808.2 may be exposed in the microwells 810. The sidewalls and peripheral edges 816 of the bottom of the microwells 810 may be covered by a second chemical 812 (non-bolded wiggly lines). The peripheral edges 816 may be portions of the bottom of the microwell 810 around the charge sensitive devices 818.1 and 808.2. The top surfaces of the chemical sensing devices 808.1 and 808.2 may be covered by a first chemical 814 (bolded wiggly lines). In one embodiment, as shown in FIG. 8, the microwells 810 may each have an inversed tapered shape. That is, the bottom of the microwells 810 may have a larger diameter than the top of the microwells 810 and thus, the sidewalls may be inversely inclined. In one embodiment, the metal oxide layer 802 may comprise one or more layers of $Ta_2O_5$, $HfO_2$, $ZrO_2$, or $Al_2O_3$; the microwell layer 806 may be a layer of $SiO_2$; and the CMOS device layer 806 may be a layer of semiconductor material (e.g., Si). The microwells 810 may be etched using directional etching, reactive ion etching, sacrificial layer etching, or combination thereof.

Figure 9E:
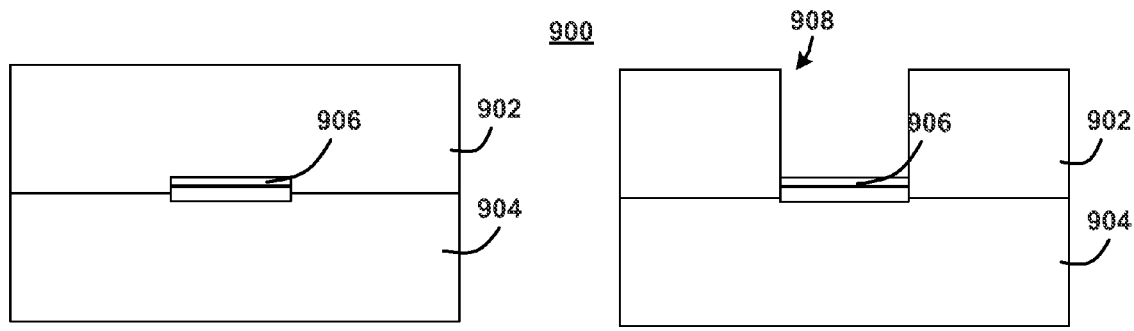
Figure 9E:
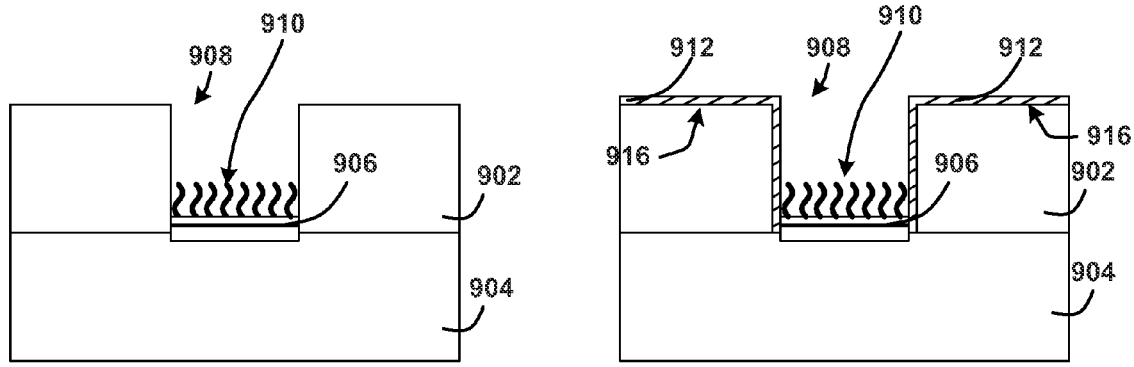
Figure 9E:
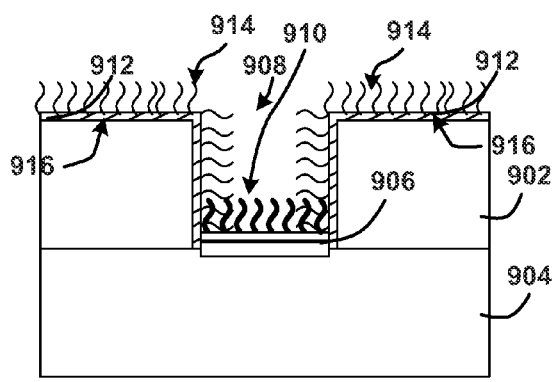

FIGS. 9A-9E illustrate cross-sectional views of different stages of fabricating a well structure according to another embodiment of the present teachings. FIG. 9A shows a cross-sectional view of a part of a chemical sensing device 900 before any microwells are formed. The chemical sensing device 900 may comprise a microwell layer 902 on top of a CMOS device layer 904, and a charge sensitive device 906 embedded between the microwell layer 902 and CMOS device layer 904. The embedded device 906 may represent a top portion of a chemFET. For example, the embedded device 906 may be the passivation layer of a chemFET (e.g., passivation layer 116 of FIG. 1), the floating gate structure of the chemFET may be underneath the device 906 (not shown). In one embodiment, the microwell layer 902 may be a layer of $SiO_2$. Further, in one embodiment, the device 906 may comprise two or more layers of metal oxides. For example, the device 906 may comprise a top layer of $Ta_2O_5$ and a bottom layer of $Al_2O_3$. The CMOS device layer may be a layer of semiconductor material (e.g., Si).

FIG. 9B shows a cross-sectional view of the chemical sensing device 900 with a microwell 908. The microwell 908 may be etched on the microwell layer 902. In one embodiment, the microwell 908 may be etched to expose the top of the device 906. The microwells 908 may be etched by anisotropic $SiO_2$ etching. FIG. 9C shows a cross-sectional view of the chemical sensing device 900 after application of a chemical. The applied chemical, shown as the bolded wiggly lines 910, may be coated only at the bottom of the microwell 908 because of chemical properties of the surface of the charge sensitive device 906. For example, the surface of the charge sensitive device 906 may have selective affinity of phosphate or phosphonate, or a silane group. In one embodiment, the chemical may be a phosphate, phosphonate, catechol, nitrocatechol, boronate, phenylboronate, imidazole, silanol or other pH-sensing group.

FIG. 9D shows a cross-sectional view of the chemical sensing device 900 after the sidewalls and top horizontal portions 916 (also referred to herein as "top edge" or "horizontal surface proximate to top edge of sidewall") of the microwell 908 is covered by a layer 912 of metal oxide. In one embodiment, the metal oxide layer 912 may be a mono-molecular layer. For example, the mono-molecular layer may be a metal oxide formed by a chemo selective reaction of well wall oxide (such as silicon dioxide) with Zirconium alkoxides followed by hydrolysis post reaction. That is, the metal oxide layer 912 may be a layer of a solvent based deposition of ZrO$_2$. The metal oxide layer 912 is not disposed along the bottom portion of the well, as shown in FIG. 9D, due to the lack of affinity between the metal oxide layer 912 and the chemical 910, according to an embodiment of the present teachings. In effect, the chemical 910 may serve as a "mask" or a protective/barrier layer to prevent the metal oxide layer 912 from being disposed along the bottom of the microwell. FIG. 9E shows a cross-sectional view of the chemical sensing device 900 after application of another chemical. The other chemical, shown as the non-bolded wiggly lines 914, may be coated at the sidewalls and top horizontal portions of the microwell 908 because of chemical properties of the surface of the metal oxide layer 912. In one embodiment, the other chemical may be a PEG phosphate or phosphonate. To be consistent with previous embodiments, the chemical coated at the bottom of the microwell 908 may be referred to as the first chemical and the chemical coated at the sidewalls may be referred to as the second chemical.

The neutral PEG surfaces at the sidewalls of the microwell 908 may reduce, or eliminate, the proton buffering at the sidewalls. Further, the phosphate or phosphonate coated at the bottom of the microwell may give positive charge to improve bead loading or DNA primers to further boost sequencing signal-to-noise ration (SNR).

Figure 10:
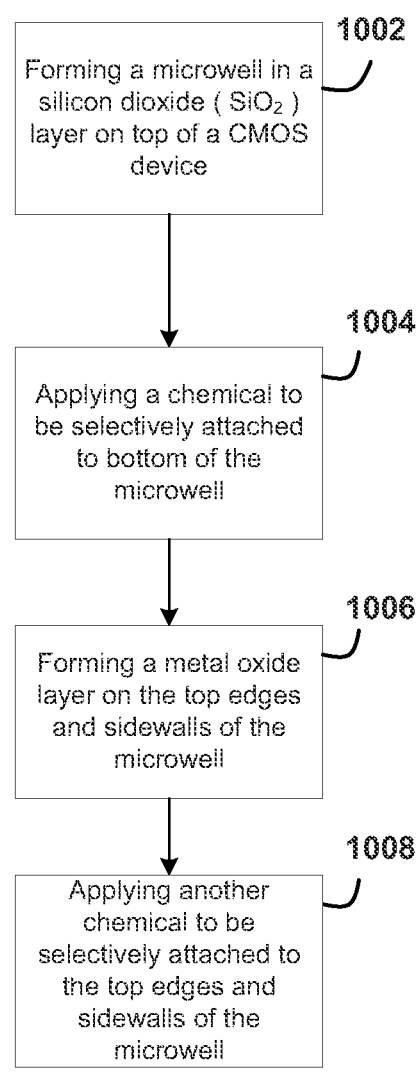
FIG. 10 illustrates a process of fabricating a well structure of FIG. 9E according to an embodiment of the present teachings.

FIG. 10 illustrates a process 1000 of fabricating a well structure of FIG. 9E according to an embodiment of the present teachings. At block 1002, a microwell may be formed in a silicon dioxide (SiO$_2$) layer on top of a CMOS device. As shown in FIG. 9B, the microwell 908 may be formed in the SiO$_2$ layer 902. Then at block 1004, a chemical may be applied to be selectively attached to the bottom of the microwell. For example, a first chemical may be applied and selectively attached to the top surface of the charge sensitive device 906 in the microwell 908. At block 1006, a metal oxide layer on the sidewalls and top horizontal portions of the microwell may be formed. As described above with respect to FIG. 9D, a solvent based deposition of ZrO$_2$ mono-molecular layer may be created at the sidewalls and top horizontal portions of the microwell 908. At block 1008, a second chemical may be applied that selectively attaches to the sidewalls and top horizontal portions of the microwell. The second chemical (e.g., the non-bolded wiggly lines 914 of FIG. 9E) may bind only to the metal oxide layer 912 of the microwell at the sidewalls and top horizontal portions, for example, because of the chemical properties of the other chemical and metal oxide layer 912.

In one embodiment, microwells may be made on a layer of metal that is placed on top of a CMOS device layer. That is, for example, the microwell layer 902 may be a layer of metal, such as, Al, Cu or Ti. In this embodiment, the bottom of the microwells may be coated by the first chemical, or the sidewalls of the microwells may be coated by the second chemical, or both. Further, in this embodiment, the top edges of the microwells may be covered by a metal oxide layer, such as one or more layers of tantalum pentoxide (Ta$_2$O$_5$), aluminum oxide (Al$_2$O$_3$), Hafnium dioxide (HfO$_2$), or zirconium oxide (ZrO$_2$). The fabrication for metal microwells may use Damascene or dual Damascene process. For example, use photolithography to make negative pillar patterns, deposit a seed layer, perform metal electrical plating, polish the metal and then etch the negative pillar patterns to form metal microwells. See, e.g., Ohmori, et al., Japanese Journal of Applied Physics 49 05FD01: 1-4 (2010), the content of which is incorporated herein by reference.

In one embodiment, the silane group for the second chemical may be R—[(CH2)n]-Si-[X1X2X3] where R is an organofunctional group, [(CH2)n] is a hydrocarbon linker (n=1 to 20) Si is a silicon atom, and [X1X2X3] comprises one or more independent hydrolysable groups, including alkoxy or halogen groups. In another embodiment, the silane group for the second chemical may be R—[(C2H4O)n]-Si-[X1X2X3] where R is an organofunctional group, [(C2H40)n] (n=1 to 100) is a polyether linker, Si is a silicon atom, and [X1X2X3] comprises one or more hydrolysable groups, including alkoxy or halogen groups. In either of the embodiments, organofunctional groups R include, but are not limited to methyl, methylene, phenyl, benzyl, anilino, amino, amide, hydroxyl, aldehyde, alkoxy, halo, mercapto, carboxy, acyl, vinyl, allyl, styryl, epoxy, isocyanato, glycidoxy, and acryloxy.

Examples of the silane group for the second chemical may include:
 N-(6-AMINOHEXYL)AMINOMETHYLTRIETHOXYSILANE,
 (MERCAPTOMETHYL)METHYLDIETHOXYSILANE,
 CHLOROMETHYLTRIETHOXYSILANE,
 (ISOCYANATOMETHYL)METHYLDIMETHOXYSILANE,
 N-PHENYLAMINOMETHYLTRIETHOXYSILANE,
 TRIETHOXYSILYLUNDECANAL,
 11-MERCAPTOUNDECYLTRIMETHOXYSILANE,
 10-UNDECENYLTRIMETHOXYSILANE,
 N-(2-AMINOETHYL)-11-AMINOUNDECYLTRIMETHOXYSILANE,
 11-BROMOUNDECYLTRIMETHOXYSILANE,
 n-OCTYLTRIETHOXYSILANE,
 2-[METHOXY(POLYETHYLENEOXY)PROPYL]TRIMETHOXYSILANE,
 3-METHOXYPROPYLTRIMETHOXYSILANE,
 METHOXYTRIETHYLENOXYPROPYLTRISILANE,
 METHOXYSILANE,
 METHOXYETHOXYUNDECYLTRICHLOROSILANE,
 2-[METHOXY(POLYETHYLENEOXY)PROPYL]-TRICHLOROSILANE.

Figure 11:
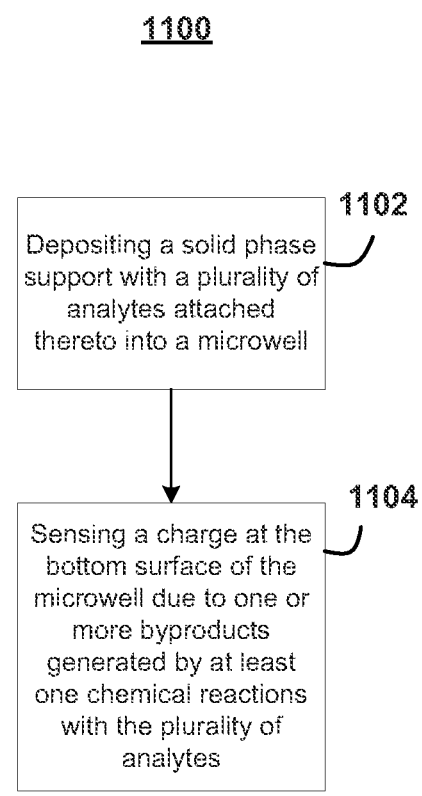
FIG. 11 illustrates a chemical sensing process according to an embodiment of the present teachings.

FIG. 11 illustrates a chemical sensing process 1100 according to an embodiment of the present teachings. At block 1102, a solid phase support with a plurality of analytes attached thereto may be deposited into a microwell. For example, a plurality of analytes may be attached to the solid phase support 112 and the solid phase support 112 may be deposited into the microwell 101. The microwell may have a bottom surface and sidewalls. In one embodiment, the bottom surface may be covered in a first chemical that facilitates pH sensing and the sidewalls may be covered in a second chemical that reduces buffering of protons in the solution. At block 1104, a charge at the bottom surface of the microwell may be sensed. As described with respect to equations (1) and (2), the charge may be due to one or more byproducts generated by at least one chemical reactions with the plurality of analytes. In one embodiment, the chemical sensing process 1100 may be a DNA sequence sensing process. That is, each of the plurality of analytes may be a sample DNA fragment. The DNA sequence may be determined by subsequently supplying different reagents to the microwell 101 and detecting byproducts of chemical reactions.

Several embodiments of the present invention are specifically illustrated and described herein. However, it will be appreciated that modifications and variations of the present invention are covered by the above teachings. In other instances, well-known operations, components and circuits have not been described in detail so as not to obscure the embodiments. It can be appreciated that the specific structural and functional details disclosed herein may be representative and do not necessarily limit the scope of the embodiments. For example, some embodiments are described using CMOS technology. A skilled artisan would appreciate that a CMOS device may be used to refer to a pure PMOS device or a pure NMOS device, or a combination of PMOS and NMOS devices.

Those skilled in the art may appreciate from the foregoing description that the present invention may be implemented in a variety of forms, and that the various embodiments may be implemented alone or in combination. Therefore, while the embodiments of the present invention have been described in connection with particular examples thereof, the true scope of the embodiments and/or methods of the present invention should not be so limited since other modifications will become apparent to the skilled practitioner upon a study of the drawings, specification, and following claims.

Various embodiments may be implemented using hardware elements, software elements, or a combination of both. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

Some embodiments may be implemented, for example, using a computer-readable medium or article which may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, Compact Disc Read Only Memory (CD-ROM), Compact Disc Recordable (CD-R), Compact Disc Rewriteable (CD-RW), optical disk, magnetic media, magneto-optical media, removable memory cards or disks, various types of Digital Versatile Disc (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

"Amplicon" means the product of a polynucleotide amplification reaction. That is, a clonal population of polynucleotides, which may be single stranded or double stranded, which are replicated from one or more starting sequences. The one or more starting sequences may be one or more copies of the same sequence, or they may be a mixture of different sequences that contain a common region that is amplified, for example, a specific exon sequence present in a mixture of DNA fragments extracted from a sample. Amplicons are formed by the amplification of a single starting sequence. Amplicons may be produced by a variety of amplification reactions whose products comprise replicates of the one or more starting, or target, nucleic acids. In one aspect, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al., U.S. Pat. Nos. 4,683,195, 4.965, 188, 4,683,202, and 4,800,159 (PCR); Gelfand et al., U.S. Pat. No. 5,210,015 (real-time PCR with "taqman" probes); Wittwer et al., U.S. Pat. No. 6,174,670; Kacian et al., U.S. Pat. No. 5,399,491 ("NASBA"); Lizardi, U.S. Pat. No. 5,854,033; Aono et al., Japanese patent publ. JP 4-262799 (rolling circle amplification); and the like. In one aspect, amplicons are produced by PCRs. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, co-factors, scavengers, and the like. A "solid phase amplicon" means a solid phase support, such as a particle or bead, having attached a clonal population of nucleic acid sequences, which may have been produced by a process such as emulsion PCR, or like technique.

"Analyte" means a molecule or biological cell of interest that directly affects an electronic sensor at a sample retaining region, such as a microwell, or that indirectly affects such an electronic sensor by a byproduct from a reaction involving such molecule or biological cell located in such a sample retaining region, or reaction confinement region, such as a microwell. In one aspect, analyte is a nucleic acid template that is subjected to a sequencing reaction which, in turn, generates a reaction byproduct, such as hydrogen ions, that affects an electronic sensor. The term "analyte" also comprehends multiple copies of analytes, such as proteins, peptide, nucleic acids, or the like, attached to solid supports, such as beads or particles. In a one embodiment, the term "analyte" means a nucleic acid amplicon or a solid phase amplicon.

"Microfluidics device" means an integrated system of one or more chambers, ports, and channels that are interconnected and in fluid communication and designed for carrying out an analytical reaction or process, either alone or in cooperation with an appliance or instrument that provides support functions, such as sample introduction, fluid and/or reagent driving means, temperature control, detection systems, data collection and/or integration systems, and the like. Microfluidics devices may further include valves, pumps, and specialized functional coatings on interior walls to, for example. prevent adsorption of sample components or reactants, facilitate reagent movement by electroosmosis, or the like. Such devices are usually fabricated in or as a solid substrate, which may be glass, plastic, or other solid polymeric materials, and typically have a planar format for ease of detecting and monitoring sample and reagent movement, especially via optical or electrochemical methods. Features of a microfluidic device usually have cross-sectional dimensions of less than a few hundred square micrometers and passages typically have capillary dimensions, e.g. having maximal cross-sectional dimensions of from about 0.1 µm to about 500 µm. Microfluidics devices typically have volume capacities in the range of from a few nL, e.g. 10-100 nL to 1 µL. The fabrication and operation of microfluidics devices are well-known in the art as exemplified by the following references that are incorporated by reference: Ramsey, U.S. Pat. Nos. 6,001,229, 5,858,195, 6,010,607, and 6,033,546; Soane et al., U.S. Pat. Nos. 5,126,022 and 6,054,034; Nelson et al., U.S. Pat. 6,613,525; Maher et al., U.S. Pat. No. 6,399,952; Ricco et al., International patent publication WO 02/24322; Bjornson et al., International patent publication WO 99/19717; Wilding et al., U.S. Pat. Nos. 5,587,128; 5,498,392; Sia et al., Electrophoresis, 24: 3563-3576 (2003); Unger et al., Science, 288: 113-116 (2000); Enzelberger et al., U.S. Pat. No. 6,960,437.

"Microwell," which is used interchangeably with "reaction chamber," means a special case of a "reaction confinement region," that is, a physical or chemical attribute of a solid substrate that permit the localization of a reaction of interest. Reaction confinement regions may be a discrete region of a surface of a substrate that specifically binds an analyte of interest, such as a discrete region with oligonucleotides or antibodies covalently linked to such surface. Usually reaction confinement regions are hollows or wells having well-defined shapes and volumes which are manufactured into a substrate. These latter types of reaction confinement regions are referred to herein as microwells or reaction chambers, and may be fabricated using conventional microfabrication techniques, for example, as disclosed in the following references: Doering and Nishi, Editors, Handbook of Semiconductor Manufacturing Technology, Second Edition (CRC Press, 2007); Saliterman, Fundamentals of BioMEMS and Medical Microdevices (SPIE Publications, 2006); Elwenspoek et al., Silicon Micromachining (Cambridge University Press, 2004); and the like. Configurations (e.g., spacing, shape and volumes) of microwells or reaction chambers are disclosed in Rothberg et al., U.S. patent publication 2009/0127589; Rothberg et al., U.K. patent application GB24611127, which are incorporated by reference. Microwells may have square, rectangular, or octagonal cross sections and be arranged as a rectilinear array on a surface. Microwells may also have hexagonal cross sections and be arranged as a hexagonal array, which permit a higher density of microwells per unit area in comparison to rectilinear arrays. Exemplary configurations of microwells have $10^2$, $10^3$, $10^4$, $10^5$, $10^6$ or $10^7$ reaction chambers.

As used herein, an "array" is a planar arrangement of elements such as sensors or wells. The array may be one or two dimensional. A one dimensional array is an array having one column (or row) of elements in the first dimension and a plurality of columns (or rows) in the second dimension. The number of columns (or rows) in the first and second dimensions may or may not be the same. The array may include, for example, at least 100,000 chambers. Further, each reaction chamber has a horizontal width and a vertical depth with, for example, an aspect ratio of about 1:1 or less. The pitch between the reaction chambers is no more than about 10 microns, for example. Briefly, in one embodiment, microwell arrays may be fabricated after the semiconductor structures of a sensor array are formed, in which the microwell structure is applied to such structure on the semiconductor die. That is, the microwell structure can be formed on the die or it may be formed separately and then mounted onto the die.

To form the microwell structure on the die, various fabrication processes may be used. For example, the entire die may be spin-coated with, for example, a negative photoresist such as Microchem's SU-8 2015 or a positive resist/polyimide such as HD Microsystems HD8820, to the desired height of the microwells. The desired height of the wells (e.g., about 3-12 µm in the example of one pixel per well, though not so limited as a general matter) in the photoresist layer(s) can be achieved by spinning the appropriate resist at predetermined rates (which can be found by reference to the literature and manufacturer specifications, or empirically), in one or more layers. (Well height typically may be selected in correspondence with the lateral dimension of the sensor pixel for a nominal 1:1-1.5:1 aspect ratio, height:width or diameter.) Alternatively, multiple layers of different photoresists may be applied or another form of dielectric material may be deposited. Various types of chemical vapor deposition may also be used to build up a layer of materials suitable for microwell formation therein. In one embodiment, microwells are formed in a layer of tetra-methyl-ortho-silicate (TEOS). The invention encompasses an apparatus comprising at least one two-dimensional array of reaction chambers, wherein each reaction chamber is coupled to a chemically-sensitive field effect transistor ("chemFET") and each reaction chamber is no greater than $10^3$ µm³ (i.e., 1 pL) in volume. Each reaction chamber is no greater than 0.34 pL, and no greater than 0.096 pL or even 0.012 pL in volume. A reaction chamber can optionally be $0.5^2$, $1$, $2^2$, $3^2$, $4^2$, $5^2$, $6^2$, $7^2$, $8^2$, $9^2$, or $10^2$ square microns in cross-sectional area at the top. The array can have at least $10^2$, $10^3$, $10^4$, $10^5$, $10^6$, $10^2$, $10^8$, $10^9$, or more reaction chambers. The reaction chambers may be capacitively coupled to the chemFETs.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following references that are incorporated by reference: Diefenbach, editor, PCR Primer: A Laboratory Manual, 2nd Edition (Cold Spring Harbor Press, New York, 2003).

What is claimed is:
1. A method of fabricating a chemical detection device, comprising:
forming a microwell in a microwell layer disposed above a CMOS device layer, wherein the microwell comprises a bottom surface and sidewalls, the bottom surface at least partially defined by a material layer over a gate terminal of a CMOS device of the CMOS device layer;
applying a first chemical to be selectively attached to the material layer of the CMOS device;

forming a metal oxide layer on the sidewalls of the microwell and not on the material layer of the CMOS device, the metal oxide layer different from a material of the microwell layer; and applying a second chemical to be selectively attached to the metal oxide layer on the sidewalls of the microwell and not on the bottom surface, wherein the second chemical lacks an affinity to the first chemical.

2. The method of claim 1, wherein the microwell layer comprises one or more top edges covered by the metal oxide layer, wherein the metal oxide layer is a mono-molecular layer.

3. The method of claim 2, wherein the second chemical includes a neutral PEG phosphate or PEG phosphonate.

4. The method of claim 2, wherein the metal oxide layer is a solvent based deposition of zirconium oxide ($ZrO_2$).

5. The method of claim 1, wherein the second chemical comprises a silane group.

6. The method of claim 1, wherein the first chemical comprises a phosphate, phosphonate, catechol, nitrocatechol, boronate, phenylboronate, imidazole, silanol.

7. The method of claim 1, wherein the first chemical comprises a pH-sensing group.

8. The method of claim 1, wherein the CMOS device comprises a charge-sensitive transistor having the gate terminal and the material layer on top of the gate terminal, the gate terminal being a floating gate terminal, the bottom surface of the microwell defined by the material layer on top of the floating gate terminal.

9. A chemical detection device, comprising:
a CMOS device layer including a CMOS device; and
a microwell layer disposed over the CMOS device layer and defining a microwell having sidewalls and a bottom surface, at least a portion of the bottom surface defined by a material layer disposed over a gate terminal of the CMOS device, the material layer covered by a first chemical, a metal oxide layer disposed on the sidewalls and not the gate terminal of the CMOS device, the metal oxide layer different from a material of the microwell layer, a second chemical disposed on the metal oxide layer and not the bottom surface, wherein the second chemical lacks an affinity to the first chemical.

10. The chemical detection device of claim 9, wherein the CMOS device comprises a charge-sensitive transistor, the gate terminal being a floating gate terminal of the charge-sensitive transistor.

11. The chemical detection device of claim 10, wherein the material layer is on top of the floating gate terminal.

12. The chemical detection device of claim 11, wherein the material layer is a layer of metal oxide different from the metal oxide layer on the sidewalls.

13. The chemical detection device of claim 9, wherein the first chemical comprises a phosphate, phosphonate, catechol, nitrocatechol, boronate, phenylboronate, imidazole, silanol.

14. The chemical detection device of claim 9, wherein the first chemical comprises a pH-sensing group.

15. The chemical detection device of claim 9, wherein the microwell layer includes $SiO_2$.

16. The chemical detection device of claim 9, wherein metal oxide layer on the sidewalls is a mono-molecular layer.

17. The chemical detection device of claim 16, wherein top edges of the microwell are covered by the metal oxide layer.

18. The chemical detection device of claim 17, wherein the metal oxide layer is a solvent based deposition of one of zirconium oxide ($ZrO_2$).

19. The chemical detection device of claim 9, wherein the second chemical is a neutral PEG phosphate or PEG phosphonate.

20. A method comprising:
forming a microwell in a microwell layer disposed above a CMOS device layer including a CMOS device, wherein the microwell comprises sidewalls and a bottom surface at least partially defined by a material layer disposed over a gate electrode of the CMOS device, the microwell is configured to receive a solid phase support that has a plurality of analytes attached thereto;
applying a first chemical to be selectively attached to the material layer of the CMOS device;
forming a metal oxide layer on the sidewalls of the microwell and not on the material layer of the CMOS device; and
applying a second chemical to be selectively attached to the metal oxide layer on the sidewalls of the microwell and not the bottom surface, wherein the second chemical lacks an affinity to the first chemical, wherein the CMOS device is configured to sense a charge at the bottom surface of the microwell based on one or more byproducts of at least one chemical reaction of the plurality of the analytes, wherein the one or more byproducts lack an affinity to the second chemical.

* * * * *